United States Patent [19]

Tominaga et al.

[11] 4,289,031
[45] Sep. 15, 1981

[54] METHOD OF MEASURING HARDNESS OF FLEXIBLE THREAD-WOUND GOLF BALLS OR INNER CORES THEREOF

[75] Inventors: Ichiro Tominaga; Teruo Sasaki, both of Kobe, Japan

[73] Assignee: Sumitomo Rubber Industries, Ltd., Hyogo, Japan

[21] Appl. No.: 89,733

[22] Filed: Oct. 31, 1979

[30] Foreign Application Priority Data

Nov. 4, 1978 [JP] Japan ............................... 53-136103

[51] Int. Cl.$^3$ .............................................. G01N 29/00
[52] U.S. Cl. ...................................... 73/597; 273/213
[58] Field of Search ................. 73/599, 600, 597, 598, 73/579; 273/213, 216, 218, 222

[56] References Cited

U.S. PATENT DOCUMENTS

| | | | |
|---|---|---|---|
| 2,175,685 | 10/1939 | Dieterich | 273/216 |
| 2,667,063 | 1/1954 | Cunningham, Jr. | 73/598 |
| 4,147,064 | 4/1979 | Bond | 73/597 |

OTHER PUBLICATIONS

H. J. Moskimin et al., "Water Immersion Tech. Measuring Attenuation and Phase Velocity of Longitudinal Waves in Plastics", *J. Acous. Soc. Am.*, vol. 49, No. 3, (Part 2), pp. 713–722, Mar. 1971.

*Primary Examiner*—Stephen A. Kreitman
*Attorney, Agent, or Firm*—Birch, Stewart, Kolasch & Birch

[57] ABSTRACT

A method of measuring hardness of a flexible thread-wound golf ball or its inner core which includes the steps of holding the flexible thread-wound golf ball or its inner core to be measured between a transmitter coupled to an ultrasonic wave oscillating source and a receiver coupled to an ultrasonic wave detecting device which detects the ultrasonic wave received by said receiver, applying from the transmitter, the ultrasonic wave having predetermined frequency to the flexible thread-wound golf ball or its inner core, and measuring the hardness of the flexible thread-wound golf ball or its inner core selectively by or based on the propagation time of the ultrasonic wave passing through the central portion of the flexible thread-wound golf ball or its inner core.

6 Claims, 4 Drawing Figures

METHOD OF MEASURING HARDNESS OF FLEXIBLE THREAD-WOUND GOLF BALLS OR INNER CORES THEREOF

BACKGROUND OF THE INVENTION

The present invention generally relates to hardness measuring and more particularly, to a method of measuring hardness of a flexible thread-wound golf ball or its inner core portion wound with flexible thread.

Commonly, the constructions of golf balls may be broadly divided into two types, i.e., one being the so-called thread-wound golf ball comprising a core portion of round shape, a flexible thread, for example, of rubber tightly wound around said core portion under the application of a tension to a certain extent to form a thread-wound inner core of the thread-wound golf ball, and an outer layer, for example, of gutta percha, plastics and the like applied onto said flexible thread for covering, and the other being the so-called solid golf ball which is made through one-piece molding, by subjecting to vulcanization during heating under pressure, a mixture including rubber, crosslinking resin, polymerization initiator and filling agent, etc. and filled in a mold. The present invention relates to a method of measuring the hardness of the thread-wound golf ball or its inner core portion wound with the flexible thread.

Although there has been no established practice for a method of measuring the hardness (sometimes referred to as "compression" by those skilled in the art) of the thread-wound golf ball or its inner core portion wound with the flexible thread so far, conventional methods normally employed therefor may be broadly classified into the following two procedures.

(i) To represent the hardness by a reaction force produced when the golf ball or its inner core is subjected to a strain by a predetermined amount.

(ii) To represent the hardness by the amount of strain when a predetermined amount of load is applied to the golf ball or its inner core.

In both of the above conventional methods of hardness measuring, the strain to be imparted and the amount of the strain consequently produced are limited only to about 5% of the maximum diameters of the golf ball and its inner core to be measured, and moreover, since the measured values obtained in the above case are markedly influenced by non-uniformity of the winding density of the flexible thread on the inner core or of elasticity modulus of the flexible thread, there is such an inconvenience that the hardness differs from spot to spot even when measurements are taken on one golf ball or its inner core, thus showing the so-called anisotropy, and the deviations in the measured hardness resulting from the anisotropy reaches as high as 10 to 20%, presenting serious problems in the hardness control of the golf balls.

On the other hand, the strain to be imparted to the golf ball during impact in actual play is by far larger than the strain produced in the hardness measurement of the golf ball, and normally amounts to 20 to 30% of the diameter of the golf ball. The hardness of the ball to be felt by the hand or "stony feeling" in the above case is not a local hardness as obtained by the conventional measuring methods, but is considered to be one closer to the average value of the hardnesses obtained on all portions of one golf ball.

Incidentally, since the hardness of the golf ball of the above described type is produced by winding the flexible thread, for example, rubber thread onto the core portion in a stretched state, the average values of the hardnesses as described above is thought to be in proportion to the energy possessed by the wound rubber thread. Therefore, if the energy possessed by the wound rubber thread can be measured by some means, more realistic or practical hardness indication with small deviations may be achieved.

With particular attention directed to the above point, the present inventors have made earnest investigations into such means as described above, and finally, come to think of utilization of ultrasonic waves for the purpose.

SUMMARY OF THE INVENTION

Accordingly, an essential object of the present invention is to provide a method of measuring hardness of a thread-wound golf ball and its inner core by which realistic or practical hardness indications are obtained in an efficient manner, at high accuracy with small deviations.

Another important object of the present invention is to provide a method as described above through utilization of ultrasonic waves, with substantial elimination of disadvantages inherent in the conventional measuring methods of the kind.

In accomplishing these and other objects, according to one preferred embodiment of the present invention, there is disclosed a method of measuring hardness of a flexible thread-wound golf ball or its flexible thread-wound core which comprises the steps of holding the flexible thread wound ball or its core to be measured between a transmitter coupled to means for oscillating ultrasonic wave and a receiver coupled to means for detecting the ultrasonic wave received by said receiver, applying from the transmitter, the ultrasonic wave having predetermined frequency, preferably in the range of 10 KHz to 500 KHz and most preferably in the range of 15 KHz to 50 KHz, to the flexible thread-wound golf ball or its core, and measuring the hardness of the flexible thread-wound golf ball or its core selectively by or based on the propagation time of the ultrasonic wave passing through the central portion of said flexible thread-wound golf ball or its core.

By the method according to the present invention as described above, an efficient method of hardness measurements for thread-wound golf balls or inner cores thereof has been presented with practical hardness indications at high accuracy.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE INVENTION

Figure 1:
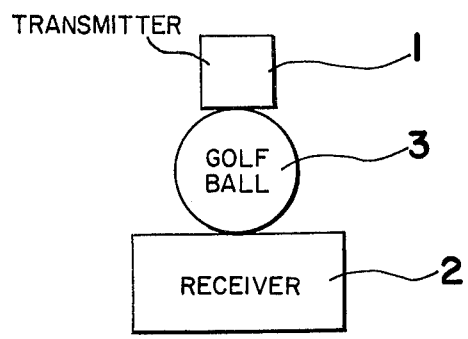
FIG. 1 is a schematic side elevational view of an arrangement which may be employed for the hardness measurement according to the present invention.

Referring now to the drawings, particularly to FIG. 1 explanatory of the principle of the hardness measurement according to the present invention, a thread-wound golf ball 3 or its inner thread-wound core 3c (FIG. 3) is held between a transmitter 1 coupled to means for oscillating ultrasonic wave (not shown) and a receiver 2 coupled to means for detecting the ultrasonic wave (not shown) received by said receiver 2, and the hardness of the thread-wound golf ball 3 or its inner thread-wound core 3c is measured by or based on the propagation time of the ultrasonic wave passing through the central portion of said golf ball 3 or its core 3c.

Figure 2:
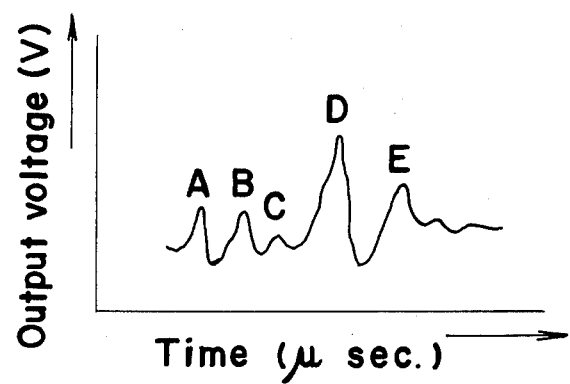
FIG. 2 is a diagram showing a waveform to be observed on an oscilloscope when ultrasonic waves are applied to a thread-wound core of a golf ball to be measured.
Figure 3:
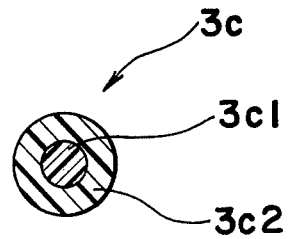
FIG. 3 is a schematic cross sectional view of the thread-wound core of the golf ball to be measured.

In FIG. 2 showing the propagation waveforms to be displayed on an oscilloscope (not shown) of the ultrasonic wave detecting means when the ultrasonic wave of 20 KHz is applied, for example, to a thread-wound core 3c including a core portion 3c1, for example, of rubber and the like about 27 mm in diameter around which a flexible rubber thread 3c2 is wound as shown in FIG. 3, and held between the transmitter 1 and receiver 2, peaks A, B and C respectively represent a longitudinal wave, a transversal wave, and a surface wave emitted from the transmitter 1 and reaching the receiver 2 after passing through the layers of the wound rubber thread 3c2, while peaks D and E denote a longitudinal wave and a transversal wave emitted from the transmitter 1 and reaching the receiver 2 through the central portion of the core portion 3c1.

Figure 4:
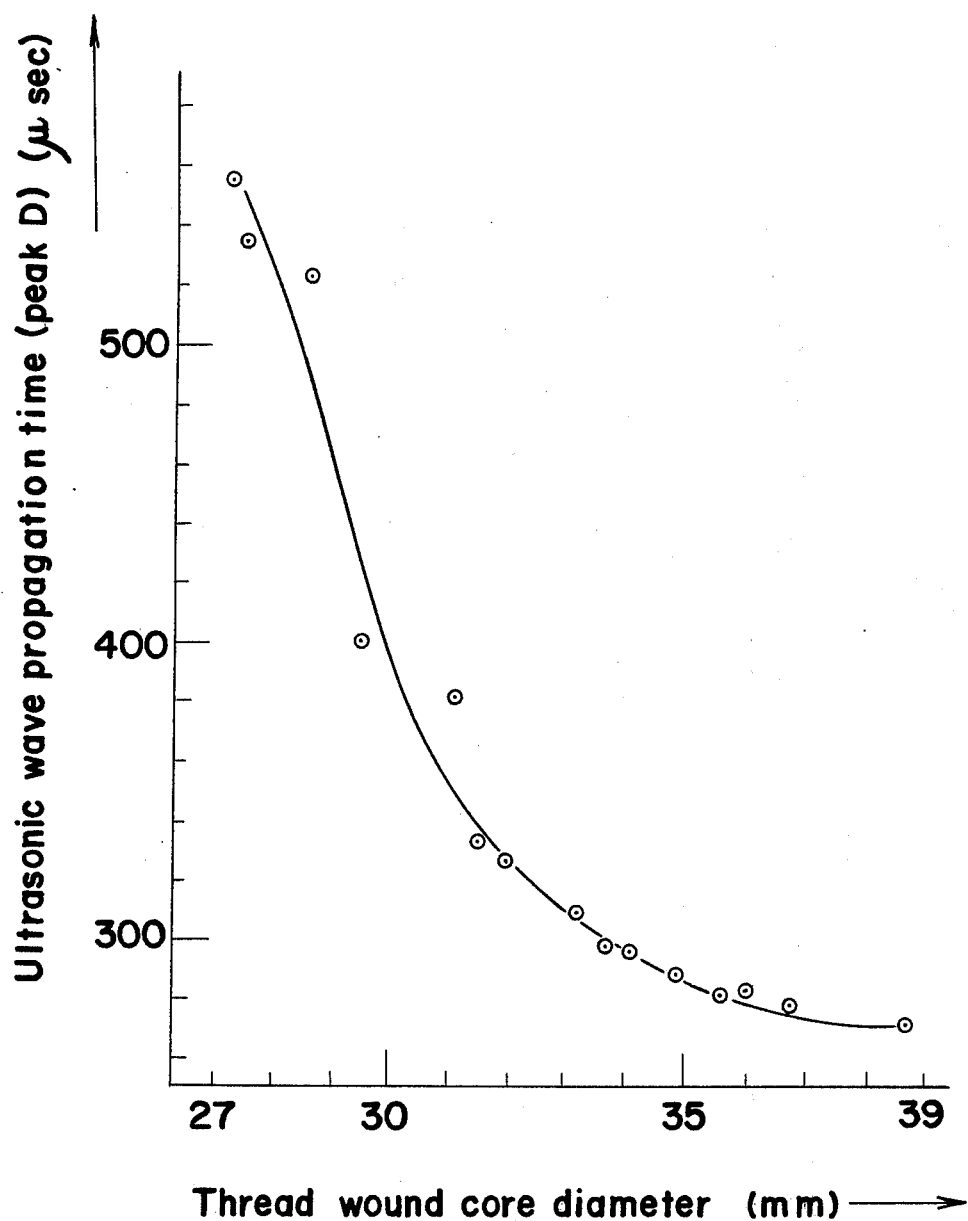
FIG. 4 is a graph showing the relation between the thread-wound core diameter and ultrasonic wave propagation time (peak D).

In FIG. 4, there is shown a state of variation of the propagation time (peak D) of the wave when the thickness of the wound rubber thread layers 3c2 is altered by unwinding the rubber thread from the outer surface of said thread-wound core 3c. The propagation time of the ultrasonic wave depends on the elasticity modulus and configuration of an object through which the ultrasonic wave passes, and despite of the fact that the propagation time is normally increased with the increase of the propagation distance, the propagation time in the case of the present invention, is increased on the contrary as the diameter of the thread-wound core is reduced so as to be ultimately converged into the propagation time of the wave propagating through the central portion of the thread-wound core.

Originally, although the core portion 3c1 itself, for example, of rubber and the like may be regarded to be very soft as considered from the long propagation time of the ultrasonic wave, it is subjected to compression by winding the rubber thread therearound at high tension, with consequent increase of the apparent elasticity modulus thereof, and as a result, the propagation time is reduced due to increase of the diameter of the inner core portion.

In FIG. 4, the propagation speed at the peak D for the thread-wound core at the diameter of 38.7 mmφ is 143 m/sec., but on the other hand, from the review on the peak A in FIG. 2, the propagation speed in the thread-wound layers is 775 m/sec., and when the fact that the thickness of said layer is approximately 12 mm (which is negligible) is taken into account, the time required for reaching the peak D is considered to depend mostly on the apparent elasticity modulus of the inner rubber core. The apparent elasticity modulus as described above is produced by the flexible thread wound onto the inner core in a stretched state, and is proportional to the energy possessed by the stretched flexible thread. Thus, in the above structure, the hardness of the ball of course depends on the propagation time for the peak D, and the hardness is to be reduced as said time increases. Accordingly, the propagation time for the peak D obtained by the ultrasonic wave projection may be utilized as the hardness indication of the thread-wound golf ball or its inner core.

Hereinbelow, EXAMPLES are given for illustrating the present invention without any intention of limiting the scope thereof.

EXAMPLE 1

With the amount of strain upon application of a predetermined load being represented by 1/1000 inch unit (the indication is, however, in number without unit) according to the conventional hardness indications for the thread-wound cores, thread-wound cores having three levels of hardness, i.e. 55, 60 and 65 and selected at width of ±1.5 for 100 pieces each were again subjected to the hardness measurement for investigation into the correlation between the average value at each of the levels and average value at each of the levels during propagation of the ultrasonic wave (20 KHz), as a result of which a correlation factor of 0.956 was obtained. Accordingly, it may be said that the selection according to the method of the present invention is closely correlated with the selection according to the conventional methods.

EXAMPLE 2

500 pieces of thread-wound cores were subjected to sifting with respect to the propagation time of 275 μsec. through utilization of the ultrasonic wave and separated into one group with the propagation time more than 275 μsec. and the other group with the propagation time less than 275 μsec. When these two groups were again measured for the propagation time by the use of the ultrasonic wave (20 KHz), the group with the propagation time less than 275 μsec. was extended in its propagation time up to the range of 275 μsec. +6 μsec., while the group with the propagation time more than 275 μsec. was also extended in its propagation time up to the range of 275 μsec. −7 μsec. The range of approximately 7 μsec. is equivalent to 1.7 in the hardness indication of the EXAMPLE mentioned earlier.

On the other hand, in the similar manner, 500 pieces of thread-wound cores were divided into two groups with respect to the sifting point 55 according to the hardness indication of EXAMPLE 1 mentioned earlier. Upon subjecting the two groups as mentioned above to the hardness measurement again, the group with the level lower than 55 was widely extended up to the hardness 55+13=68, while the other group with the level higher than 55 was also broadly extended up to the hardness 55−14=41.

In other words, according to the measuring method of the present invention, since there exists almost no anisotropy with respect to the propagation time, errors which may take place during sifting of the thread-wound golf balls are reduced to an extremely small level.

As is clear from the foregoing description, the hardness measuring method according to the present invention has advantages as follows.

(i) The measurements are taken through nondestructive test.

Although any of the conventional methods in which pressure is applied to the golf balls tends to soil the surfaces of the golf balls or damage the thread-wound cores, the method according to the present invention is free from such soiling or damages, since the golf balls or thread-wound cores only contact the transmitter and receiver during the measurements.

(ii) As described earlier, since the propagation time of the ultrasonic wave depends on the energy possessed by the wound flexible thread, hardness sufficiently averaged can be obtained.

(iii) Moreover, since there is almost no anisotropy with respect to the propagation time as mentioned earlier, errors taking place during sifting of the thread-wound golf balls or thread-wound cores are reduced to a large extent.

Although the present invention has been fully described by way of example with reference to the attached drawings, it is to be noted that various changes and modifications are apparent to those skilled in the art. Therefore, unless otherwise such changes and modifications depart from the scope of the present invention, they should be construed as included therein.

What is claimed is:

1. A method of measuring hardness of a flexible thread-wound golf ball which comprises the steps of holding the flexible thread wound golf ball to be measured between a transmitter coupled to means for oscillating ultrasonic wave and a receiver coupled to means for detecting the ultrasonic wave received by said receiver, applying from said transmitter, the ultrasonic wave having predetermined frequency to said flexible thread-wound golf ball, and measuring the hardness of said flexible thread-wound golf ball selectively by or based on the propagation time of the ultrasonic wave passing through the central portion of said flexible thread-wound golf ball.

2. A method as claimed in claim 1, wherein said frequency of the ultrasonic wave to be applied to said flexible thread-wound golf ball is in the range of 10 KHz to 500 KHz.

3. A method as claimed in claim 1, wherein said frequency of the ultrasonic wave to be applied to said flexible thread-wound golf ball is in the range of 15 KHz to 50 KHz.

4. A method of measuring hardness of a flexible thread-wound core of a flexible thread-wound golf ball which comprises the steps of holding the flexible thread-wound core to be measured between a transmitter coupled to means for oscillating ultrasonic wave and a receiver coupled to means for detecting the ultrasonic wave received by said receiver, applying from said transmitter, the ultrasonic wave having predetermined frequency to said flexible thread-wound core, and measuring the hardness of said flexible thread-wound core selectively by or based on the propagation time of the ultrasonic wave passing through the central portion of said flexible thread-wound core.

5. A method as claimed in claim 4, wherein said frequency of the ultrasonic wave to be applied to said flexible thread-wound core is in the range of 10 KHz to 500 KHz.

6. A method as claimed in claim 4, wherein said frequency of the ultrasonic wave to be applied to said flexible thread-wound core is in the range of 15 KHz to 50 KHz.

* * * * *